United States Patent [19]

Hung

[11] Patent Number: 4,994,386

[45] Date of Patent: Feb. 19, 1991

[54] PRODUCTION OF HBLV VIRUS IN THE HSB-2 CELL LINE

[75] Inventor: Chia-ling Hung, Darnestown, Md.

[73] Assignee: Pharmacia Diagnostics, Inc., Fairfield, N.J.

[21] Appl. No.: 72,354

[22] Filed: Jul. 13, 1987

[51] Int. Cl.$^5$ .......................... C12N 7/00; C12N 7/02; C12N 5/00; C12N 5/02

[52] U.S. Cl. .................. 435/235.1; 435/235; 435/239; 435/240.2; 435/240.25

[58] Field of Search ...................... 435/235, 239, 240.2, 435/240.25

[56] References Cited

U.S. PATENT DOCUMENTS 4,623,622 11/1986 Anderson ............................ 435/948

OTHER PUBLICATIONS

"Isolation of New Virus, HBLV, in Patients with Lymphoproliferative Disorders", Salahuddin et al., Science, vol. 234, pp. 596–601 (Oct. 31, 1986).

"Genomic Analysis of the Human B–Lymphotropic Virus (HBLV)", Josephs et al., Science, vol. 234, pp. 601–603 (Oct. 31, 1986).

"Mystery Disease at Lake Tahoe Challenges Virologists and Clinicians", Barnes, Science, vol. 234, pp. 541–542 (Oct. 31, 1986).

"Studies on Human Leukemic Cells in Vitro", Foley et al., pp. 65–97 in The Proliferation and Spread of Neoplastic Cells (1968).

ATCC Catalog entry for ATCC CCL 120.1 CCRF-HSB-2, pp. 81–82.

"Mutation in the VP-1 Gene is Responsible for the Extended Host Range of a Monkey B–Lymphotropic Papovavirus Mutant Capable of Growing in T–Lymphoblastoid Cells", Kanda et al., Journal of Virology, vol. 59, pp. 531–534 (Aug. 1986).

"A Viral Enhancer Element Specifically Active in Human Haematopoietic Cells", Mosthaf et al., Nature, vol. 315, pp. 597–600 (Jun. 1985).

*Primary Examiner*—Elizabeth C. Weimar
*Assistant Examiner*—Suzanne Ziska
*Attorney, Agent, or Firm*—Davis, Hoxie Faithfull & Hapgood

[57] ABSTRACT

A method of producing Human B-Lymphotropic Virus (HBLV) in the HSB-2 cell line.

7 Claims, No Drawings

PRODUCTION OF HBLV VIRUS IN THE HSB-2 CELL LINE

FIELD OF THE INVENTION

The invention relates to the in vitro cultivation of Human B-Lymphotropic Virus (HBLV) in the CCRF-HSB-2 (HSB-2) human T-lymphoblastoid cell line.

BACKGROUND OF THE INVENTION

The discovery of a new virus, HBLV, was published in "Isolation of a New Virus, HBLV, in Patients with Lymphoproliferative Disorders" Salahuddin et al. *Science* Vol. 234, p. 596 (Oct. 31, 1986). A companion article, "Genomic Analysis of the Human B-Lymphotropic Virus (HBLV)" Josephs et al., id. at 601, provided additional evidence that HBLV is a novel human Herpesvirus.

The connection between HBLV and human disease is not firmly established. HBLV may have a role in some lympho-proliferative and immune system disorders, particularly autoimmune disease conditions. It may be responsible for some rare forms of human cancer such as B-cell lymphomas. HBLV may be associated with chronic mononucleosis-like syndrome, as suggested by "Mystery Disease at Lake Tahoe Challenges Virologists and Clinicians" Barnes, id. at 541.

The HBLV primarily infects human B lymphocytes, which are part of the human white-cell immune system. In the past, the HBLV virus was obtained through culture of freshly-isolated human B lymphocytes from adult peripheral blood, bone-marrow or spleen cells or from freshly isolated phytohemagglutinin-stimulated human lymphocytes from umbilical cord blood.

The virus destroys the cells it infects in vitro. This characteristic presented an obstacle to further study of the virus and to production of a sufficient quantity of the virus for use in biochemical characterizations and diagnostic tests. Only a small amount of HBLV could be grown in tissue culture before cell destruction terminated the viral production process.

With the exception of the umbilical cord blood lymphocytes, B-lymphocytes from other human sources are frequently infected with the Epstein-Barr virus, another member of the Herpesvirus family. This coinfection makes B-lymphocytes from the adult sources less-desirable target cells for production of HBLV.

Therefore, only fresh human umbilical cord lymphocytes were used for the cultivation of HBLV. Human umbilical cord lymphocyte availability is limited, preparation for tissue culture production is complicated and the yield of lymphocytes per cord is typically low and extremely variable. Furthermore, cords must be collected and processed within 24 hours. For example, using the cord blood procedure for tissue culture production of HBLV, a typical human umbilical cord yielded 10 ml of cord blood with $1 \times 10^6$ lymphocytes per ml. This amount of lymphocytes yielded about 10-20 ml of supernatant culture fluid containing HBLV at a concentration of about $10^7$ virus particles per ml after 7 days in tissue culture. Total yield of virus was $1\text{-}2 \times 10^8$ particles per cord blood donor. The cord blood procedure is an impractical method for production of other than tiny quantities of HBLV for some research purposes, and is difficult or impossible to scale-up.

SUMMARY OF THE INVENTION

The human cell line HSB-2, when infected with HBLV, provides useful quantities of the virus. The HBLV-infected HSB-2 cell line provides a source for in vitro cultivation, allowing production of sufficient quantities of HBLV to more fully characterize the virus and to develop and demonstrate human diagnostic tests for it.

DETAILED DESCRIPTION

The invention is a procedure for the productive infection of the HBLV virus into HSB-2, which is a permanent human tissue culture cell line. The HBLV-infected HSB-2 cell line provides a vehicle for large-scale culture of HBLV virus. Sufficient quantities of the HBLV virus are produced to allow for its characterization by protein purification, nucleic acid purification, infection studies in test animals and in vitro infection studies on other human target cells. Moreover, the characterized HBLV virus may be used for the development and demonstration of human diagnostic tests where HBLV's role in some lympho-proliferative, immune or neurologic abnormalities of man may be demonstrated.

The cell line CCRF-HSB-2 may be obtained commercially from the American Type Culture Collection (ATCC) located in Rockville, Md. The ATCC catalog number is CCL 120.1. This T-lymphoblastoid cell line was derived and described by G. E. Foley et al. in "Studies on Human Leukemic Cells in Vitro" in *The Proliferation and Spread of Neoplastic Cells.* The HSB-2 cell line has been redeposited with the ATCC as accession number CRL9481. HBLV-virus per se, or from HBLV-infected human umbilical cord lymphocytes in culture or from HSB-2 cells may be used as the source of HBLV inoculum. The HBLV-infected human umbilical cord lymphocyte is described in the Salahuddin and Josephs *Science* articles cited above, and was obtained from Dr. Robert C. Gallo of the National Institutes of Health. The HBLV-infected HSB-2 cell line has been deposited with the ATCC as accession number VR2177.

The HSB-2 cells are grown in tissue culture. In the culture Production/Infection protocol below, uninfected HSB-2 cells are infected with HBLV by mixing them with infected HSB-2 cells. Infected HSB-2 cells may be obtained by mixing uninfected HSB-2 cells with infected cord lymphocytes or by mixing uninfected HSB-2 cells with supernatant from either an infected cord lymphocyte cell culture or an infected HSB-2 cell culture. If infected cord lymphocytes are used, they are mixed under the same conditions as given below in the Production/Infection disclosure for infected HSB-2 cells. If supernatant from an infected cord or HSB-2 cell culture is used, 1 ml of HBLV culture supernatant containing $10^7$ virus particles is added to $10^6$ uninfected HSB-2 cells in 5 mls of medium.

The HBLV produced in the HSB-2 cell line is harvested from tissue culture and, if desired, the virus may be concentrated by high-speed centrifugation (such as sucrose density gradient centrifuge banding), or by ultra-filtration or by precipitation methods.

For some types of diagnostic tests, harvesting and concentration of the virus are not necessary. For example, in an immunofluorescence assay (IFA) test procedure the viral substrate would be HSB-2 cells infected with the HBLV virus.

Procedures for tissue culture, infection and harvesting are given below.

TISSUE CULTURE

Uninfected HSB-2 cells are grown in RPMI 1640 tissue culture medium with 10% heat-treated fetal bovine serum added. The suspended cells in fluid medium are cultured in roller bottles. Each plastic roller bottle has a surface area of 850 cm$^2$ and may contain up to 500 ml of cell suspension. The cells are grown in an incubator at 37° C.

The viable cell number doubles in about 48 hours, up to a maximum cell number of approximately $2 \times 10^6$ cells per ml. The HSB-2 cells in culture may be treated with polybrene (4 microgram/ml) for 30 minutes at 37° C., in order to make them more susceptible to infection.

The following culture protocol is an example of how UNINFECTED HSB-2 cells may be cultured (per roller bottle):

Day 1:

(a) Harvested 300 ml ($3 \times 10^8$ cells) from 400 ml total culture volume.

(b) Centrifuged and resuspended cells in 150 ml fresh culture media. (Added these resuspended cells to the Infected HSB-2 Culture (on Day 1, step b of the infected HSB-2 culture protocol).

(c) Added 100 ml of fresh culture medium to the remaining cells (100 ml).

Day 5:

(d) Added 200 ml of fresh culture medium.

(e) Continued culture for 2 days and then repeated steps a through e.

PRODUCTION/INFECTION

The uninfected HSB-2 cells are mixed with HBLV-infected, HSB-2 cells at a ratio of 10:1, for example, $1.0-1.5 \times 10^6$ uninfected cells to $1.0-1.5 \times 10^5$ HBLV-infected cells per ml.

The following culture protocol is an example of how INFECTED HSB-2 cells may be cultured:

Day 1:

(a) Harvested 400 ml of HBLV-infected HSB-2 cell culture from 500 ml total culture volume. Removed the cells by centrifugation and collected the HBLV in the supernatant fluid.

(b) To the remaining 100 ml of HBLV-infected HSB-2 cell culture, added 150 ml of uninfected HSB-2 culture (from Day 1, step b of the uninfected HSB-2 culture protocol).

Day 5:

(c) Added 250 ml of fresh culture medium.

(d) Cultured for 2 days and then repeated steps a through d.

One roller bottle culture of HSB-2 cells infected with HBLV yielded 500 ml of culture fluid containing HBLV at a concentration of $10^7$ viral particles per ml after 7 days of culture. Total yield of virus was $5 \times 10^9$ particles per roller bottle which is approximately 25-50 times more HBLV virus than is obtained from one human umbilical donor sample.

CONCENTRATION AND PARTIAL PURIFICATION OF HBLV VIRUS BY GRADIENT CENTRIFUGATION

The HBLV-infected culture (taken from Day 1, step a of the infected cell protocol) was clarified by low-speed centrifugation to remove infected cells and debris. The resulting cell culture harvest fluid was used as the starting sample for equilibrium density banding centrifugation. Centrifugation was performed in an RK centrifuge with a J1 rotor. The linear density gradient was formed with 380 mls of 20% w/w and 400 mls of 55% w/w sucrose, buffered with TNE buffer (10mM Tris, pH 7.4, 0.1M sodium chloride, 0.001 mM EDTA). Rotor speed was 45,000 rpm and the sample flow rate was 5 l/hr.

The entire centrifuged volume was collected in 25 ml fractions and the density of each fraction was determined by its refractive index. Three pools were selected by fraction density: Pool A 1.135-1.170 gms/ml, Pool B 1.175-1.210 gms/ml, and Pool C 1.220-1.260 gms/ml. The pools were diluted with phosphate buffered saline (PBS) at pH 7.2 and pelleted in a Beckman Ti45 rotor at 20,000 rpm for 120 minutes. The pellets were resuspended in PBS; Pool A (1.135-1.170 gms/ml) was resuspended to 2 mls, Pool B (1.175-1.210 gms/ml) was resuspended to 1 ml and Pool C (1.220-1.260 gms/ml) was resuspended to 0.5 ml. The three pools collected from this operation contained fractions of the HBLV virus concentrate.

The procedure given above is one specific example of concentration and purification by gradient centrifugation. Other variants of this procedure can also be used. For example, the sucrose gradient can be replaced by other gradient materials such as Renografin ™.

MULTIPLICITY OF INFECTION AND KINETICS OF INFECTION

Multiplicity of infection (MOI) is the number of infectious virus particles added per number of target cells used for infection. $10^7$ HBLV particles per ml of culture fluid containing $10^6$ HSB-2 cells is therefore a MOI of 10. The HSB-2 cell line in culture was very susceptible to HBLV infection at this MOI, and yielded a productive infection that was observable after 4 days in culture. At that time, 30% of the HSB-2 cells were shown to be infected with HBLV by IFA and by the characteristic cell rounding and enlargement. This result indicated a substantial degree of viral infectivity and, therefore, that the HSB-2 cell line could be used to provide large quantities of HBLV.

By day 7 post-infection, the HSB-2 cell culture showed large, refractile cells, typical of infection with HBLV. By day 9 post-infection, 100% of the HSB-2 target cells were positive for HBLV infection by the IFA test. The HSB-2 cells eventually died through virus-cell cytopathology by day 16 post-infection.

The MOI by HBLV for HSB-2 cells can be reduced to as low as 0.01 virus per cell, but when this was done the complete infection of the HSB-2 cells by HBLV was delayed until day 19 post-infection as judged by cell morphology and IFA.

The following experiments were performed to confirm that HBLV infection had occurred:

INFECTION OF HSB-2 CELLS

HBLV from human cord lymphocyte culture supernatant was infected into HSB-2 cells. After infection the cells showed morphological changes similar to those shown by cord lymphocytes infected with HBLV. Specifically, the cells showed rounding and enlargement at four days post-infection, and appeared as large refractile cells at seven days post-infection. Assay by the IFA technique using HBLV patient serum showed a positive reaction on the HSB-2/HBLV cells similar to that shown by human cord lymphocytes infected with HBLV, namely, diffuse staining of the entire cell.

INFECTION OF HUMAN CORD LYMPHOCYTES WITH SUPERNATANT

Supernatant fluid from cultured HSB-2 cells infected with HBLV was infected back into human cord lymphocytes. The cord lymphocytes changed morphologically, to a condition similar to the original infected culture used in the preceding experiment. An IFA assay on these cord lymphocytes was positive for the presence of HBLV. A large number of extra-cellular HBLV particles was observed by electron microscopy (negative stain) examinations.

These results show that HBLV was: (1) reproducing in the HSB-2 cells, (2) shed by HSB-2 cells into the culture fluid, and (3) viable and capable of infecting human cord lymphocytes.

INFECTION OF HSB-2 CELLS WITH SUPERNATANT

Supernatant fluid obtained as described in the preceding experiment was infected into fresh HSB-2 cells. Again, the result was that the HSB-2 cells were infected with HBLV from the cord lymphocyte culture supernatant, as demonstrated by morphological change and IFA. The result was also confirmed by electron microscopy: thin-section analysis of the infected HSB-2 cells detected a virus with the same morphological characteristics as the virus seen in the original HBLV culture and in cultured blood cells from patients.

INFECTION OF HUMAN CORD LYMPHOCYTES WITH SUPERNATANT

Supernatant fluid obtained from the infected HSB-2 cells of the preceding experiment was infected into human cord lymphocytes in culture. Again, the cord lymphocytes underwent a morphological change similar to that shown by the original infected culture and the IFA was positive. These results indicate that HBLV was productively infected into HSB-2 cells and was the same virus as the one infecting the original human cord blood lymphocytes.

What is claimed is:

1. A method of producing HBLV comprising culturing HBLV in HSB-2 cells having the identifying characteristics of ATCC No. CRL 9481.

2. A method according to claim 1 comprising infecting HSB-2 cells in culture with HBLV and growing said cells under conditions suitable for production of said virus.

3. A method according to claim 2 wherein said infecting comprises mixing uninfected HSB-2 cells with HBLV-infected HSB-2 cells.

4. A method according to claim 1 wherein the cells are cloned from ATCC No. CRL 9481.

5. A method according to claim 2 wherein said infecting comprises mixing uninfected HSB-2 cells with HBLV-containing supernatant collected from HBLV-infected HSB-2 cell culture.

6. A method according to claim 1 further comprising harvesting the virus from the HSB-2 cell line culture.

7. HSB-2 cell line infected with HBLV, deposited as ATCC VR2177.

* * * * *